United States Patent
Morita et al.

(10) Patent No.: US 6,211,415 B1
(45) Date of Patent: Apr. 3, 2001

(54) PROCESS FOR THERMAL DECOMPOSITION OF HEXAFLUOROPROPYLENE OXIDE OLIGOMERS

(75) Inventors: Shigeru Morita; Toshihiko Amano, both of Osaka (JP)

(73) Assignee: Daikin Industries, Ltd., Osaka (JP)

( * ) Notice: Subject to any disclaimer, the term of this patent is extended or adjusted under 35 U.S.C. 154(b) by 0 days.

(21) Appl. No.: 09/308,587

(22) PCT Filed: Nov. 21, 1997

(86) PCT No.: PCT/JP97/04256

§ 371 Date: May 21, 1999

§ 102(e) Date: May 21, 1999

(87) PCT Pub. No.: WO98/22422

PCT Pub. Date: May 28, 1998

(30) Foreign Application Priority Data

Nov. 22, 1996 (JP) .................................................... 8-312244

(51) Int. Cl.[7] .................................................... C07C 43/11
(52) U.S. Cl. ........................................... 568/615; 568/621
(58) Field of Search ...................... 568/615, 621

(56) References Cited

U.S. PATENT DOCUMENTS 4,769,184 * 9/1988 Okabe et al. .................... 260/544 F

FOREIGN PATENT DOCUMENTS

| 46-27172 | 8/1971 | (JP) . |
|---|---|---|
| 49-45719 | 12/1974 | (JP) . |
| 54-109918 | 8/1979 | (JP) . |
| 57-31633 | 2/1982 | (JP) . |
| 61-225146 | 10/1986 | (JP) . |
| 62-120335 | 6/1987 | (JP) . |
| 63-77835 | 4/1988 | (JP) . |
| 222245 | 1/1990 | (JP) . |
| 225439 | 1/1990 | (JP) . |
| 273034 | 3/1990 | (JP) . |
| 2218641 | 8/1990 | (JP) . |
| 6306010 | 11/1994 | (JP) . |

OTHER PUBLICATIONS

Martini, Perfluorierte Olefins . . . Ketone, Tetrahedron Letters, No. 22, pp. 1861–1864, May 1976.*
Zakharova, V. Yu. et al. (1994) 30 (12) pp. 1844–1846.
Chen L.S. et al. (1991) 55(1) pp. 93–100.

* cited by examiner

*Primary Examiner*—Rosalynd Keys
(74) *Attorney, Agent, or Firm*—Birch, Stewart, Kolasch, Birch, LLP

(57) ABSTRACT

A hexafluoropropylene oxide oligomer of the formula: $RfO[CF(CF_3)CF_2O]_nCF(CF_3)COF$ in which Rf is a group represented by the formula: $F(CF_2)_m-$ in which m is an integer of 1 to 8, or the formula: $(CF_3)_2CF(CF_2)q-$ in which q is an integer of 0 to 6, and n is a number of 3 to 20 is heated and thermally decomposed in a solvent at a temperature of at least 100° C. in the presence of a compound which generates a fluoride ($F^-$) ion to obtain mainly the dimer, trimer and tetramer of hexafluoropropylene oxide. Thus, the valuable low molecular weight oligomers of hexafluoropropylene oxide can be obtained from high molecular weight oligomers of hexafluoropropylene oxide which have been discarded.

8 Claims, No Drawings

US 6,211,415 B1

PROCESS FOR THERMAL DECOMPOSITION OF HEXAFLUOROPROPYLENE OXIDE OLIGOMERS

This application is the national phase under 35 U.S.C. §371 of prior PCT International Application No. PCT/JP97/04256 which has an International filing date of Nov. 21, 1997 which designated the United States of America.

FIELD OF THE INVENTION

The present invention relates to a process of the preparation of the dimer, trimer and tetramer of hexafluoropropylene oxide (hereinafter referred to as "HFPO"), having high utility values by the thermal decomposition of HFPO oligomers which are prepared by the oligomerization of HFPO.

HFOP oligomers (dimer, trimer and tetramer) are transferred to vinyl ethers, which are used as modifiers for fluororesins, or as the raw materials of high-performance fluororubbers.

PRIOR ART

Among HFPO oligomers, a dimer (a compound of the below-described formula (I) in which n is 0) is thermally decomposed to give perfluoropropyl vinyl ether. The copolymerization of perfluoropropyl vinyl ether and tetrafluoroethylene gives a fluororesin, which is called "PFA". The copolymerization of tetrafluoroethylene and a perfluorovinyl ether, which is obtained by the thermal decomposition of a HFPO tetramer (a compound of the below-described formula (I) in which n is 2), gives a perfluororubber having good chemical resistance and also good cold resistance.

When HFPO is polymerized in the presence of a catalyst such as CsF, etc. to obtain such vinyl ethers, the product has a molecular weight distribution. For example, when a dimer is prepared, the produced dimer contains 5 wt. % or more of a trimer. If the preparation of oligomers having high molecular weights is planned, the proportion of undesirable higher molecular weight products further increases.

It is impossible to completely avoid the formation of such by-products having higher molecular weights because of the properties of oligomerization reactions, but many reports are found in literatures to selectively synthesize oligomers having desired molecular weights. Nevertheless, it is impossible to completely avoid the formation of by-products having higher molecular weights, even if various ideas are put into the preparation processes. Thus, a large amount of by-products inevitably generate when HFPO oligomers are produced in an industrial scale. Such by-products decrease the unit of intended products. Furthermore, the waste disposal involves a high cost. In addition, if wastes are disposed of by incineration, environmental pollution such as air pollution may be induced.

SUMMARY OF THE INVENTION

The present invention intends to provide a process to completely and effectively revive by-products having higher molecular weights, which are inevitably produced due to the natures of processes, to valuable components.

Accordingly, the present invention provides a process for the thermal decomposition of a hexafluoropropylene oxide oligomer of the formula:

$$RfO[CF(CF_3)CF_2O]_nCF(CF_3)COF \quad (I)$$

wherein Rf is a group represented by the formula:

$$F(CF_2)_m-$$

in which m is an integer of 1 to 8, or the formula:

$$(CF_3)_2CF(CF_2)_q-$$

in which q is an integer of 0 to 6, and n is a number of 3 to 20 comprising the step of heating the oligomer in a solvent at a temperature of at least 100° C. in the presence of a compound which generates a fluoride (F⁻) ion.

The present invention also provides for a process wherein the hexafluoropropylene oxide oligomer of the formula (I) contains other oligomers of hexafluoropropylene oxide.

When a high molecular weight compound of the formula (I) is heated at a temperature of at least 100° C. in the presence of an alkali metal fluoride such as CsF, it can be decomposed as desired to give the useful dimer, trimer and tetramer of HFPO, and also high purity $CF_3CF_2COF$ which is a raw material used in oligomerization reactions.

DETAILED DESCRIPTION OF THE INVENTION

A catalyst to be used in the thermal decomposition process of the present invention may be any catalyst, insofar as it can generate a fluoride (F⁻) ion in principle like a catalyst which is used to polymerize HFPO. A catalyst is selected by taking into account an affinity to a solvent and handling easiness. Preferable examples of catalysts are alkali metal fluorides such as cesium fluoride, alkaline earth metal fluorides, organic fluorides, etc. Specific examples of catalysts include NaF, KF, RbF, CsF, $MgF_2$, $CaF_2$, $SrF_2$, etc.

The amount of a catalyst is from 0.01 to 10 wt. %, preferably from 0.1 to 5 wt. %, more preferably from 0.2 to 2 wt. %, based on the weight of HFPO oligomers.

Solvents are used to effectively carry out the thermal decomposition of the oligomers. Preferably, solvents, in which the above catalysts can be dissolved, are used. Preferable examples of solvents are glymes of the formula:

$$CH_3O(CH_2CH_2O)_pCH_3$$

wherein p is 2, 3 or 4
(e.g. diglyme, triglyme, tetraglyme, etc.), aprotic polar solvents (e.g. dimethylformamide (DMF), dimethylacetamide (DMA), dimethylsulfoxide (DMSO), hexamethylphosphonylamide (HMPT), etc.), and the like. A solvent is selected by taking into account the molecular weights (or boiling points) of oligomers to be treated, the boiling points of regenerated products, decomposition reaction temperature, etc.

The amount of a solvent is from 10 to 300 wt. parts, preferably from 50 to 150 wt. parts, more preferably from 50 to 100 wt. parts, per 100 wt. parts of the HFPO oligomers.

The decomposition temperature is at least 100° C., preferably at least 150° C., although it depends on the molecular weights (or boiling points) of oligomers to be treated. It may be necessary to heat oligomers at a temperature of 200° C. or higher to start the decomposition of the oligomers, when the oligomers contain water, hydrofluoric acid, carboxylic acids which are formed by the reaction of water and acid fluorides, etc. When water is contained, perfluorovinyl ethers may form in the early stage of thermal decomposition. In many cases, such perfluorovinyl ethers are high molecular weight ones, which are undesired. Thus, the mixing of water in a thermal decomposition system should be avoided as much as possible.

Compounds generated from the thermal decomposition include oligomers the molecular weights of which are decreased, and $CF_3CF_2COF$, and they are recovered in the form of vapors from a reaction system. In the recovering step of products, distillates are preferably refluxed to effectively recover desired components. That is, when a refluxing temperature is adjusted around the boiling temperature of a desired oligomer, a distillate containing the desired oligomer in a high concentration can be effectively obtained. However, when the difference of the molecular weights of oligomers to be treated and that of a desired oligomer is large, the amount (or percentage) of generated $CF_3CF_2COF$ increases, and thus a refluxing temperature shifts. Therefore, the refluxing temperature should be carefully monitored.

It is possible to recover all the raw material oligomers as $CF_3CF_2COF$ under certain conditions. When the amount of low boiling components increases, it is necessary to take necessary measures such as pressurization to maintain a reaction temperature high.

The reaction pressure is not critical, and may vary from reduced pressure to elevated pressure depending on the boiling points of oligomers to be treated, or the boiling temperatures of regenerated products.

EXAMPLES

Example 1

A still residue, which was formed by distilling off required components from a mixture obtained by the oligomerization of HFPO, [contained components:

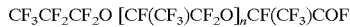
$CF_3CF_2CF_2O\,[CF(CF_3)CF_2O]_n CF(CF_3)COF$ in which the weight ratio of the product of n being 2 to that of n being 3 to that of n being 4 is 0.12:92.7:5.5] (100 ml) was poured into a 300 ml glass flask, and CsF (1 g) and

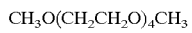
$CH_3O(CH_2CH_2O)_4CH_3$ (tetraglyme) (100 ml) were charged. Then, the mixture was gradually heated.

When the internal temperature of the flask reached 204° C., the mixture began to boil. Shortly after that, the mixture sent out white smoke, and began to more vigorously boil, while the internal temperature of the flask gradually decreased.

The products were distilled off through a vacant column having a height of 20 cm. During the distillation, the head temperature of this column was 160° C., while the temperature of the flask was 200° C.

The distillates were condensed with a Liebig condenser, and uncondensed gas was trapped with a dry iced trap. About eighty grams of the condensed products were recovered.

The condensed products were analyzed by gas chromatography, and the products were compounds of the formula:

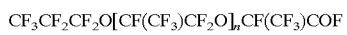
$CF_3CF_2CF_2O[CF(CF_3)CF_2O]_n CF(CF_3)COF$ in which the weight ratio of the compound of n being 0 to that of n being 1 to that of n being 2 to that of n being 3 to that of n being 4 was 9.2:9.5:32.3:47.5:1.5.

The amount of products trapped in the dry iced trap was about 10 ml, most of which was gas having a boiling point of about −30° C. This gas was confirmed to be $CF_3CF_2COF$ by IR analysis.

Example 2

The same still residue was distilled in the same manner as in Example 1 except that the head temperature was maintained at 120° C. through the adjustment of heating of flask.

The condensed products were analyzed by gas chromatography, and the products were compounds of the formula:

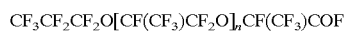
$CF_3CF_2CF_2O[CF(CF_3)CF_2O]_n CF(CF_3)COF$ in which the weight ratio of the compound of n being 0 to that of n being 1 to that of n being 2 to that of n being 3 to that of n being 4 was 11.8:26.8:41.4:19.5:0.45.

Example 3

The same still residue was distilled in the same manner as in example 2 except that a head temperature was maintained at a temperature shown in Table 1, and the distilled products were analyzed by gas chromatography. The results are shown in Table 1.

TABLE 1

| Head temp. (° C.) | Still temp. (° C.) | n = 0 (%) | n = 1 (%) | n = 2 (%) | n = 3 (%) |
|---|---|---|---|---|---|
| 65 | 196 | 98.2 | — | — | — |
| 83 | 182 | 6.72 | 76.6 | 10.47 | 0.69 |
| 93 | 185 | 5.30 | 61.96 | 24.97 | 1.37 |
| 110 | 194 | 1.99 | 23.45 | 63.68 | 5.48 |
| 122 | 194 | 1.84 | 21.62 | 62.70 | 7.00 |
| 129 | 195 | 1.59 | 17.29 | 64.11 | 11.31 |
| 138 | 194 | 2.94 | 22.99 | 51.20 | 17.42 |
| 148 | 192 | 1.69 | 18.20 | 50.97 | 25.84 |
| 156 | 192 | 1.16 | 13.37 | 45.71 | 36.30 |

Comparative Example 1

The same still residue was distilled in the same manner as in example 1 except that the still residue was heated at a temperature in the range between 206° C. and 210° C. in the absence of tetraglyme. In this Comparative Example, no white smoke generated, although the reaction time was prolonged.

The distillates were compounds of the formula:

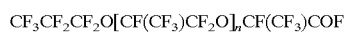
$CF_3CF_2CF_2O[CF(CF_3)CF_2O]_n CF(CF_3)COF$ in which the weight ratio of the compound of n being 0 to that of n being 1 to that of n being 2 to that of n being 3 to that of n being 4 was 0:0:0.24:95.8:3.5.

This result means that substantially no raw material was decomposed, although the composition of components slightly changed due to distillation.

Example 4

Tetraglyme (1.5 liters), CsF (0.08 kg) and the same still residue as that used in Example 1 (7.5 kg) were charged in a 10 liter glass flask, and heated up to 200° C. while stirring. When the temperature reached 200° C., the decomposition reaction started, and also the refluxing started. The thermal decomposition was continued, while controlling the heating of the flask so that the temperature of refluxed portions was maintained at 130° C. The reaction temperature gradually decreased to 180° C. The distillates were trapped by flowing them through a water-cooled condenser, and untrapped distillates were trapped with a dry iced trap.

When the thermal decomposition ceased after 7 hours from the start of the decomposition reaction, the same still residue (7.5 kg) was supplemented, and CsF (0.03 kg on the average) and tetraglyme (0.21 liter) were also supplemented to continue the reaction. The supplement and reaction were repeated 40 times in total. That is, 275.7 kg of the still residue was treated, and 198.7 kg of distillates was recovered. The averaged values of the results are shown in Table 2.

TABLE 2

|  | At the start | Supplement | Average/batch |
|---|---|---|---|
| Still residue | 7.5 kg | 7.5 kg | 7.5 kg |
| CsF | 0.08 kg | 0.03 kg | 0.036 kg |
| Tetraglyme | 1.5 liters | 0.21 liter |  |
| Time |  |  | 7 hours |
| Distillates |  |  | 5.4 kg |
| Contents of distillates |  |  |  |
| $CF_3CF_2COF$ |  | 3.25% | 2.1 kg |
| n = 0 |  | 3.80% | 0.21 kg |
| n = 1 |  | 32.00% | 1.73 kg |
| n = 2 |  | 51.49% | 2.78 kg |
| n = 3 |  | 8.83% | 0.48 kg |

What is claimed is:

1. A process for the thermal decomposition of a hexafluoropropylene oxide oligomer of the formula:

$$RfO[CF(CF_3)CF_2O]_nCF(CF_3)COF \quad (I)$$

wherein Rf is a group represented by the formula:

$$F(CF_2)_m-$$

in which m is an integer of 1 to 8, or the formula:

$$(CF_3)_2CF(CF_2)_q-$$

in which q is an integer of 0 to 6, and n is a number of 3 to 20 comprising the step of heating the oligomer in a solvent at a temperature of at least 100° C. in the presence of a compound which generates a fluoride (F−) ion.

2. A process according to claim 1, wherein said compound which generates a fluoride ion is an alkali metal fluoride.

3. A process according to claim 2, wherein said alkali metal fluoride is cesium fluoride.

4. A process according to claim 1, wherein said solvent is a glyme.

5. A process according to claim 4, wherein said solvent is a compound of the formula:

$$CH_3O(CH_2CH_2O)_pCH_3$$

wherein p is 2, 3 or 4.

6. A process according to claim 1, wherein said hexafluoropropylene oxide oligomer of the formula (I) contains other oligomers of hexafluoropropylene oxide.

7. A process for harvesting $$RfO(CF(CF_3)CF_2O)_n CF(CF_3)COF,$$

wherein Rf is a group represented by the formula:

$$F(CF_2)_m-$$

in which m is an integer of 1 to 8, or the formula:

$$(CF_3)_2CF(CF_2)q-$$

in which q is an integer of 0 to 6, n is an integer of 0 to 2, and $$CF_3CF_2COF$$

from the thermal decomposition of a hexafluoropropylene oxide oligomer of the formula:

$$RfO(CF(CF_3)CF_2O)_nCF(CF_3)COF \quad (I)$$

wherein Rf is a group represented by the formula:

$$F(CF_2)_m-$$

in which m is an integer of 1 to 8, or the formula:

$$(CF_3)_2CF(CF_2)q-$$

in which q is an integer of 0 to 6, and n is a number of 3 to 20, comprising the steps of:
(a) heating the oligomer in a solvent at a temperature of at least 100° C. in the presence of a compound which generates a fluoride (F−) ion
(b) distilling and condensing a product obtained from step (a), and
(c) recovering said product obtained from step (b).

8. The process for harvesting $$RfO(CF(CF_3)CF_2O)_nCF(CF_3)COF$$

according to claim 7, wherein the Rf of $$RfO(CF(CF_3)CF_2O)_nCF(CF_3)COF \text{ is } CF_3CF_2CF_2.$$

* * * * *